United States Patent
Burgard

(10) Patent No.: US 6,632,233 B1
(45) Date of Patent: Oct. 14, 2003

(54) RESECTION INSTRUMENT

(76) Inventor: Gunther Burgard, Fasanenweg 7, Homburg (DE)

( * ) Notice: Subject to any disclaimer, the term of this patent is extended or adjusted under 35 U.S.C. 154(b) by 0 days.

(21) Appl. No.: 09/763,107

(22) PCT Filed: Apr. 13, 1999

(86) PCT No.: PCT/EP99/02484

§ 371 (c)(1),
(2), (4) Date: Mar. 26, 2001

(87) PCT Pub. No.: WO00/10470

PCT Pub. Date: Mar. 2, 2000

(30) Foreign Application Priority Data

Aug. 19, 1998 (DE) ..................... 298 14 889 U

(51) Int. Cl.[7] ............................... A61B 17/32
(52) U.S. Cl. ..................................... 606/169
(58) Field of Search ............... 30/27, 317, 329; 606/1, 167, 170, 169, 171, 15, 41, 45, 46, 180, 27; 604/27, 35, 22, 46, 170.03, 164.06, 272–274; 607/138; 600/564, 565

(56) References Cited

U.S. PATENT DOCUMENTS

| | | | | |
|---|---|---|---|---|
| 783,359 A | * | 2/1905 | Bowden | 30/317 |
| 1,489,603 A | * | 4/1924 | Kracht | 30/27 |
| 4,040,414 A | * | 8/1977 | Suroff | 601/2 |
| 4,383,530 A | * | 5/1983 | Bruno | 604/274 |
| 4,791,924 A | * | 12/1988 | Kelman | 606/1 |
| 4,832,683 A | * | 5/1989 | Idemoto et al. | 433/119 |
| 4,834,729 A | * | 5/1989 | Sjostrom | 604/22 |
| 5,117,822 A | * | 6/1992 | Laghi | 604/113 |
| 5,201,731 A | * | 4/1993 | Hakky | 600/461 |
| 5,295,980 A | * | 3/1994 | Ersek | 604/272 |
| 5,327,896 A | * | 7/1994 | Schmieding | 600/566 |
| 5,345,940 A | * | 9/1994 | Seward et al. | 600/439 |
| 5,348,023 A | * | 9/1994 | McLucas | 30/325 |
| 5,456,689 A | * | 10/1995 | Kresch et al. | 606/180 |
| 5,527,331 A | * | 6/1996 | Kresch et al. | 606/180 |
| 5,741,287 A | * | 4/1998 | Alden et al. | 604/22 |
| 5,916,173 A | * | 6/1999 | Kirsner | 600/547 |
| 5,954,713 A | * | 9/1999 | Newman et al. | 606/15 |
| 6,066,153 A | * | 5/2000 | Lev | 606/180 |
| 6,193,653 B1 | * | 2/2001 | Evans et al. | 600/210 |

* cited by examiner

Primary Examiner—Michael J. Hayes
Assistant Examiner—Cris L. Rodriguez

(57) ABSTRACT

A resection instrument, especially for the minimally invasive, subanodermal, submucous removal of hemorrhoidal tissue, comprises a narrow oblong carrier provided with a resection portion for removing tissue on a front part. In order to improve a resection instrument such that tissue can be resected precisely and as gently as possible by handling the instrument in the easiest possible way it is suggested according to the invention that the resection portion has a trough-like bulge being curved in a convex manner and approximately spoon-shaped in the longitudinal section, with a resection surface provided with a resection element being disposed on the inner side of the trough-like bulge.

17 Claims, 3 Drawing Sheets

RESECTION INSTRUMENT

Figure 1:
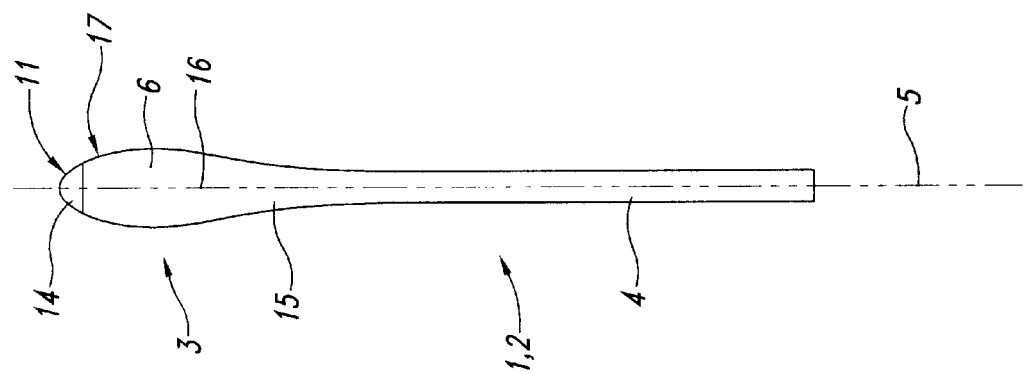

The invention relates to a resection instrument, especially for the minimally invasive, subanodermal, submucous removal of hemorrhoidal tissue comprising a narrow oblong carrier means provided with a resection portion for removing tissue on a front part.

Resection instruments for removing parts of tissue during operations at the human body are sufficiently known from the prior art. They have the purpose of separating tissue and removing it from the body. Especially during minimally invasive operations resection instruments have gained an increasing importance, since they allow the selective separation and removal of tissue through smallest body openings within the body in a very precise manner.

Resection instruments are, for example, used for the minimally invasive, subanodermal, submucous removal of hemorrhoidal tissue, whereby the narrow oblong resection instrument is introduced at the point between the anoderm and the skin of the buttock such that the sensitive anoderm is hardly injured. The hemorrhoidal tissue is dissected and fragmented underneath the anoderm by means of ultrasound and resected with the resection instrument only afterwards.

On a resection instrument of the above-mentioned type known from G 298 03 143 is provided a tissue-removing resection cutting means at a front end of the carrier means. The cutters extend through the carrier means and are approximately disposed in the area of cutter openings distributed on the surface area over the circumference of the carrier means. Said resection instrument has on principle proved to be reliable. If it is applied with care and practice in the handling thereof, the tissue can be locally resected with great precision.

The invention is based on the object to improve the resection instrument of the aforementioned type such that tissue can be resected precisely and as gently as possible by simultaneously handling the instrument in the easiest possible way. According to the invention said object is provided with a resection instrument of the aforementioned type characterized in that the resection portion has a trough-like bulge being curved in a convex manner and approximately spoon-shaped in the longitudinal section, with a resection surface provided with a resection means being disposed on the inner side of the trough-like bulge.

The curved, spoon-shaped, trough-like bulge provides for a kind of cavity in which the resection takes place. The instrument can be controlled such that only the parts of the tissue to be removed are passed to the region of the cavity and to the resection surface. The trough-shaped bulge forms kind of a protection so that surrounding parts of tissue are not affected. The tissue is protected on the rear side of the bulge facing away from the inner side, which allows to precisely move along tissue parts with the rear side and to selectively treat bad tissue on the inner side of the instrument.

The trough-like bulge can extend along the carrier means approximately only in a one-dimensional direction. It may optionally also be designed in a spherical manner.

By means of the resection portion designed according to the invention tissue can be resected with great precision, whereby adjacent healthy parts of tissue are hardly affected. The handling of said instrument is very easy.

When using it as hemorrhoidal resection instrument, the instrument is introduced at a small incision in the fringe area between the anoderm, which is the transitional skin at the end of the channel of the anus between the mucosa of the rectum and the outer skin of the buttock, and is moved forward with the rear side of the bulge being adjacent to the anoderm. On the resection surface being adjacent to the inner side of the trough-like bulge hemorrhoidal tissue is removed by means of the resection means. The hemorrhoidal tissue is usually dissected and fragmented with a vibration-surgical unit beforehand.

The carrier means may advantageously comprise an approximately rod-shaped holding portion, which extends in the longitudinal direction, and the trough-like bulge may, deviating from the longitudinal direction, be designed in a fashion that it at least partly bends back to the longitudinal direction in a convex manner. The holding portion extending in the longitudinal direction serves the orientation for the alignment of the resection portion. Deviating from the longitudinal direction the resection surface is then provided in the trough-like bulge in a fashion slightly displaced backwards, so that a localization of the bulge is possible from outside. By means of the bulge bending back to the longitudinal direction the approximately spoon-shaped form is obtained in the longitudinal cross-section, which can be controlled by the handling portion such that only tissue to be removed is passed into the area of the resection surface.

The trough-like bulge does not necessarily have to bend back to the longitudinal direction. Although this configuration is possible, the end of the bulge may also end in a fashion spaced apart from the longitudinal direction. Longitudinal direction preferably relates to a straight line. Likewise conceivable is, for example, also a slightly arch-shaped configuration of the holding portion, whereby the holding portion may also have a short stub-like shape.

According to an advantageous embodiment the bulge may have, starting at the holding portion, a first arch curved outwardly and deviating from the longitudinal direction and, joining the same, a second arch bent in a direction opposite to the first arch, at the inner side of which facing the longitudinal direction at least a part of the resection surface is provided. By means of the first arch the holding portion deviates from the longitudinal direction. Opposite thereto is provided the second arch forming the main part of the bulge and at the inner side of which is provided the resection surface inclined towards the longitudinal direction. The arches may optionally be circular with their central points being arranged on different sides of the instrument, which forms the opposite bending of the radii. The configuration by means of the arches is particularly favorable in view of gentle transitions along the instrument so as to allow the forward movement thereof through a small incision into a body cavity without difficulties.

The resection surface may favorably be limited exclusively to the area of the second arch. Thus, the resection surface is localized with precision and disposed in a protected manner within the through-like bulge in its entire area.

In a special manner at least one suction opening may be provided approximately in the area of the resection surface, which can be connected to a negative pressure source. The tissue to be resected is sucked through the suction opening into the bulge towards the resection portion so that it can be resected. The particularly refers to loose, e.g. pre-fragmented tissue parts. Important healthy parts of the tissue such as muscles, particularly in a tensioned state, are not sucked and, therefore, remain at a distance from the bulge and are not drawn into the cavity.

At least in the area of the bulge the resection portion may optionally be broader than the holding portion. Thus, the area of the cavity can be made to have a larger surface. In a body lumen the resection portion may be applied to a larger surface while the holding portion may have a relatively narrow design for passing the instrument through a smallest possible body cavity.

As a variant of the invention the bulge may have a flat configuration in the cross-section relative to a holding portion of the carrier means. The flat configuration allows the bulge to be easily inserted into narrow body gaps, whereby adjacent tissue is hardly affected.

According to a preferred embodiment a light-dispensing means may be provided on the rear side of the resection portion facing away from the inner side. The light emitted from the light-dispensing means can be used by the operating surgeon as positioning aid. The light has a diaphanoscopic effect—it transmits light through the tissue parts towards the rear side. By means of the light and the shade contours of the surrounding tissue the operating surgeon recognizes the position of the resection portion. The rear side is usually provided close to the outer surface of the body so that the position of the instrument can be recognized due to the light-dispensing means and the instrument can be controlled accordingly. Especially with hemorrhoidal resections the rear side of the resection portion is approximately adjacent to the anoderm, and by means of the light shining through the anoderm the exact position of the resection portion can be recognized.

A light-dispensing means may advantageously be provided at a front end of the resection portion. This arrangement allows the location of the front area of the instrument to be recognized so that the operating surgeon obtains information on the forward movement of the instrument in the body.

In a special manner at least the front end of the resection portion may be provided with an ultrasound unit for dissecting and fragmenting tissue, whereby, in a vibration-surgical manner, the tissue can be dissected and fragmented. In a hemorrhoidal operation the hemorrhoidal tissue may be isolated from the inner sphincter on one side and from the anoderm on the other side. The anoderm thereby remains preserved and the musculus internus undamaged.

As a surgical ultrasonic tool a frequency of, for example, 20,000 to 40,000 hertz may be applied. Thus the hemorrhoidal tissue can be dissected and fragmented selectively and without damaging the healthy tissue. In the following it can be disintegrated and removed by means of the resection means with the result that it can be removed from the area between the sphincter and the anoderm piece by piece.

In accordance with a special embodiment the resection portion may be constructed as an ultrasonic vibration tissue disintegration device for dissecting and fragmenting tissue. If the resection portion itself is constructed as an ultrasonic unit practically the entire resection portion or the entire instrument vibrates so that surrounding bad tissue is dissected while healthy tissue is not affected.

The resection portion may possibly be provided with a rinsing opening joining a rinsing channel to be connected to a rinsing system. Rinsing fluid can be fed via the rinsing opening or optionally it can also be discharged. Thus the area to be treated can be rinsed and possibly freely moving tissue parts can be detached. As rinsing fluid or rinsing medium, for example, physiological salt solution or Ringer's lactate solution respectively may be applied via the opening. Especially when applying electro-vaporization (tissue vaporization) as resection method this is particularly favorable. The rinsing fluid can either flow back through a rinsing channel of the instrument or escape at the incision point between skin and instrument. For feeding rinsing fluid back also the suction opening may be used. The rinsing fluid may also be used for cleaning the resection means, for example, if the resection opening is apt to be clogged by tissue parts. The rinsing may optionally also be used for cooling purposes.

According to a special embodiment of the invention the rinsing opening may at least area-wise be provided in the resection surface.

Figure 2:
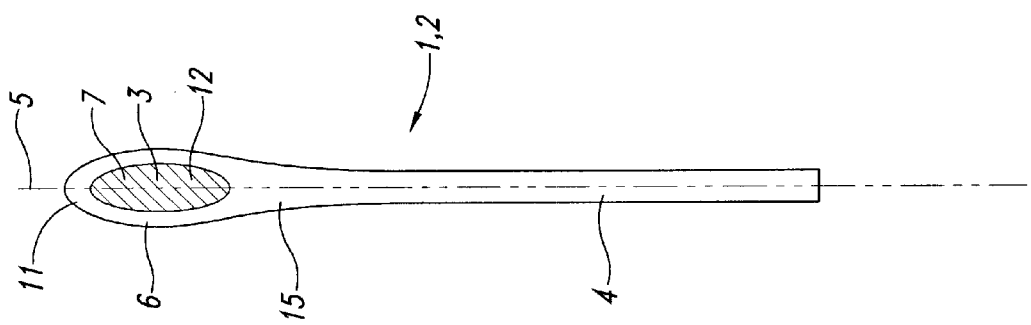
Figure 3:
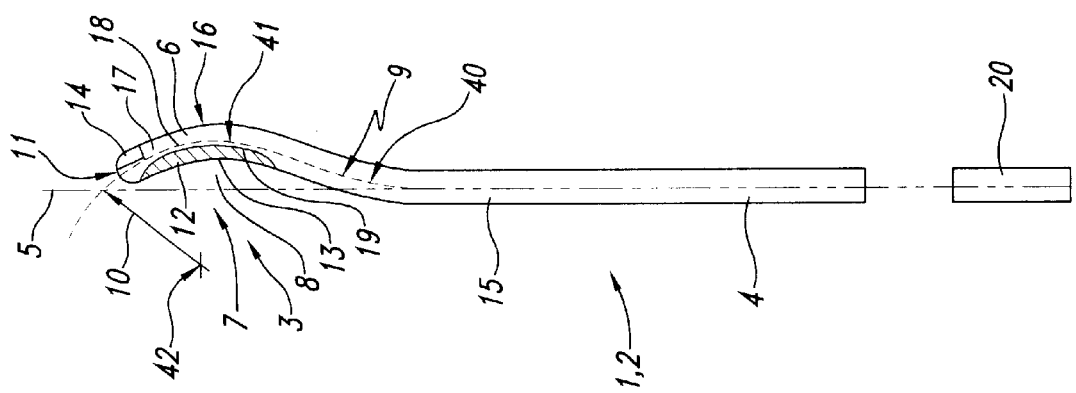
Figure 4:
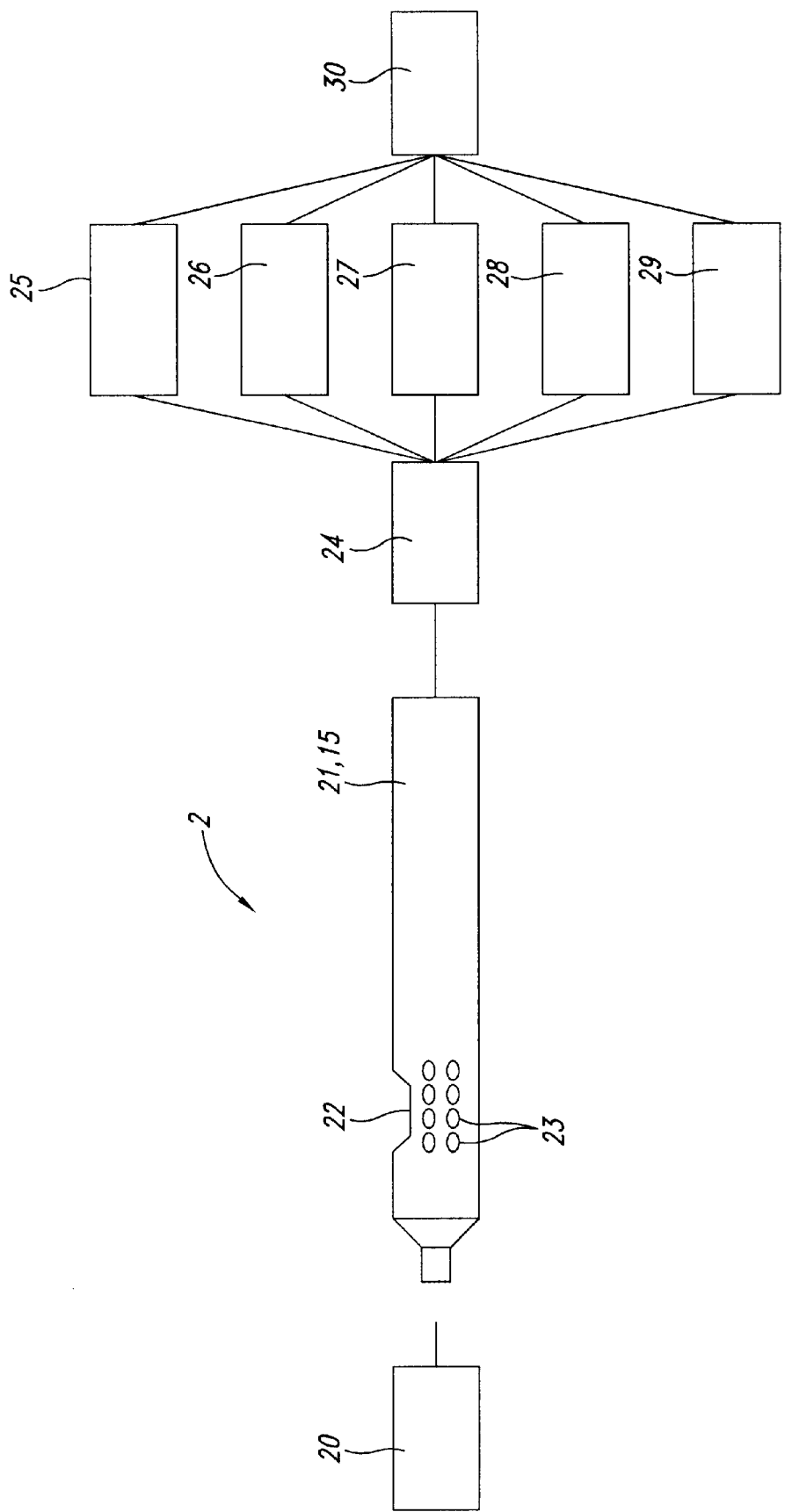
Figure 5:
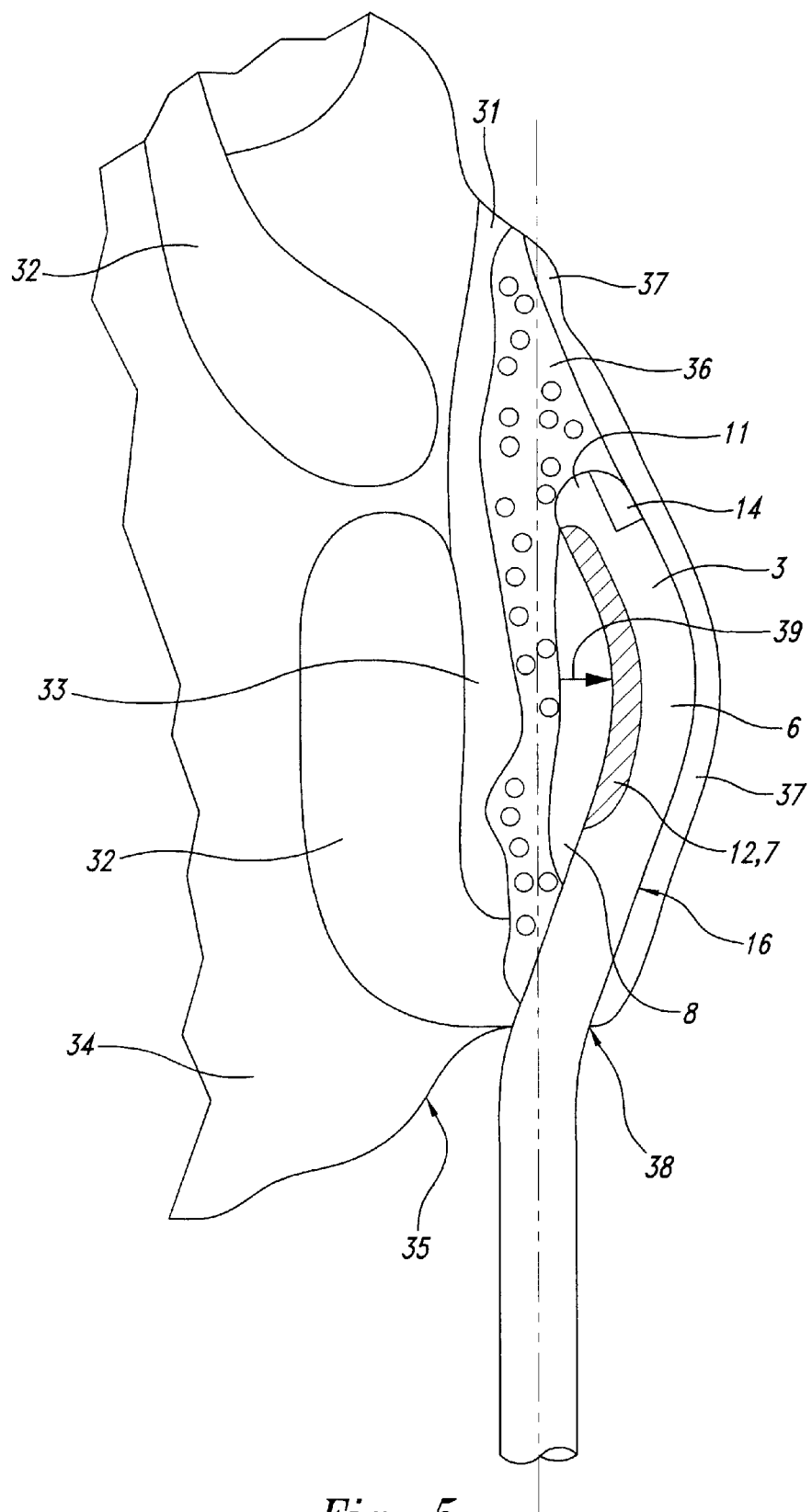

An embodiment of the invention is illustrated in the drawing and will hereinafter be explained, wherein FIG. 1 shows a lateral view onto a first part of a resection instrument according to the invention, FIG. 2 shows a bottom view onto the resection instrument illustrated in FIG. 1, FIG. 3 shows a top view onto the rear side of the resection instrument illustrated in FIG. 1, FIG. 4 shows a schematic outline of a holding portion with connectable supply units of a resection instrument according to the invention, and FIG. 5 shows a schematic illustration of a resection instrument according to the invention in the rectum area when hemorrhoidal tissue is removed.

FIG. 1 illustrates a first part 1 of a resection instrument 2 according to the invention in a lateral view. FIG. 2 shows the first part in a folded illustration, so that one directly looks on the bottom side of instrument 2. In FIG. 3 the instrument 2 shown in FIG. 1 is illustrated in a position folded towards the other direction, so that one directly looks on the rear side of instrument 2.

The first part 1 of the resection instrument 2 illustrated in FIGS. 1 to 3 comprises a narrow oblong carrier means 15 with a resection portion 3 and a holding portion 4. The holding portion is approximately designed in a rod-shaped manner and extends along a longitudinal direction 5 in the form of a straight line. The longitudinal direction 5 may also be slightly bent in another embodiment.

The carrier means 15 is hollow so that the devices required for the resection can extend therethrough up to their working area in resection portion 3.

The resection portion 3 is adjacent holding portion 4, whereby the resection portion deviates from the longitudinal direction 5 and has a bulge 6, which in a lateral view approximately has the shape of a trough. The bulge 6 is convex and is approximately spoon-shaped in a longitudinal section comprising the longitudinal direction 5. The bulge forms a cavity 8 on the inner side 7 facing the elongated longitudinal direction The form of the resection portion 3 is brought about by two arches 40, 41 of two radii. The first arch 40 deviates from the longitudinal direction 5 outwardly and has a first radius 9. The convex trough-shaped part of the resection portion, i.e. the bulge 6, is formed by the second arch 41 of a second radius 10, the central point of which, according to FIG. 1, is located on a side of the resection instrument 2 opposite to the central point 42 of the first radius 9. Thus, a double oppositely wound form of the resection portion 3 is obtained, which is composed of two arches 40, 41 having opposite curvatures.

The foremost end 11 of the bulge 6 is designed to be bent towards the longitudinal direction 5. It ends at the distance from the longitudinal direction 5. Optionally an embodiment may be chosen, where the bulge 6 or the foremost end 11 extends back to the longitudinal direction 5.

A resection surface 12 is arranged on the inner side 7 of the bulge 6. The resection surface 12 exclusively extends in the area formed by the second radius 10. It is provided on the inner side 7 approximately oblong and in a mouth-shaped manner. A resection means 13 is provided in the area of the resection surface 12. It may consist, for example, of a means for electro-vaporization, a means for high-frequency technology, a laser, a water beam device or a mechanical resection means such as a rotating knife, i.e. a cutting device. The resection surface 12 is preferably designed as a resection opening, in which, for example, a rotating knife as cutting device serves to resect the tissue.

When using an electro-vaporization device, a kind of tissue vaporizer, it is advisable to use a physiological salt solution or Ringer's lactate solution as rinsing medium. With the electro-vaporization device tissue can in principle be dissolved or vaporized respectively by means of bipolar electro-surgery.

As is shown in FIG. 2 the resection portion in the area of the bulge 6 is broader than the holding portion 4. The width of the resection portion 3 corresponds to approximately 0.75 to 1 cm. The bulge 6 has a flat configuration relative to the holding portion 4 in the cross-section comprising radii 9, 10.

At the foremost end 11 of the bulge 6 a light-dispensing means 14 is provided. The light dispensing means 14 emits diaphanoscopically utilizable light. It is preferably configured as a cold light source, e.g. as a glass fiber light conductor, which extends through the carrier means 15 and emits light towards the outside at the foremost end 11.

The light-dispensing means 14 emits light from the rear side 16 facing away from the inner side 7 of the bulge 6. The light-dispensing means 14 is thereby provided on the rear side 16 located opposite of the resection surface 12 and emits light from this point.

The entire resection portion is designed as an ultrasonic vibration tissue disintegration device for dissecting and fragmenting tissue, which means that the entire resection portion or, respectively, said part of the carrier means 15 may be caused to vibrate so as to pre-dissect the bad tissue. Optionally only the front end 11 of the resection portion is configured as an ultrasonic unit or is provided with an integrated ultrasonic device. A working surface of the ultrasonic unit may thereby be provided at the front end 11, which dissects the tissue while the instrument advances. Usually frequencies of 20,000 to 40,000 hertz are applied for the ultrasound.

The resection surface is designed as resection opening 12, which simultaneously serves as suction opening 18. The suction opening can thereby extend over the entire resection surface 12 or only over a part thereof. The suction opening 18 can be connected to a negative pressure source, which is supplied with negative pressure via a suction channel extending in the carrier means 15 to the suction opening 18.

The resection portion comprises a rinsing opening 19 joining a rinsing channel to be connected to a rinsing system. The rinsing channel extends through the carrier means 15. The rinsing opening 19 may extend over the entire resection surface 12 or only over a part thereof.

The bulge 6 may also have a spherical shape so that it is very similar to a spoon-shape and forms a three-dimensional arch.

As is shown in FIGS. 1 to 3, the front end 11 may have a round or angular, rather spattle-like shape.

In FIG. 1 a connecting member 20 is illustrated, by means of which the first part 1 may be connected to a second part 21 configured as handling portion. The second part 21 is illustrated in FIG. 4.

The handling portion 21 is provided with a marking 22 molded into the outer side in the form of a recess with a plurality of handle knobs 23 being provided around the area of the marking 22.

As is schematically illustrated the instrument 2 is provided with a foot control 24 by means of which the ultrasound unit 17 and/or the resection means 13 can be switched on and off independently of each other. Also the sucking function and/or the rinsing function can possibly be controlled therewith.

A driving means 25 for the resection means 13, a vibration drive 26 for the ultrasound unit 17, the suction pump 27, the rinsing system 28 and a light source 29 are illustrated in the form of a block. All of said devices may be controlled by microprocessor 30.

FIG. 5 shows a cross-section through a part of the human rectum area with a rectum 31, an outer sphincter 32, an inner sphincter 33, subcutaneous fatty tissue 34 and outer skin 35 of one buttock. In the area of the anal opening an enlarged hemorrhoidal complex 36 is located on the left-hand side. The hemorrhoidal tissue 36 is located underneath the anoderm 37 forming the skin between the skin of the buttock and the inner mucosa of the rectum. The anoderm 37 has highly sensitive nerves and cares for the sensoric continence.

An incision 38 is produced between the anoderm 37 and the skin 35 of the buttock, through which the resection instrument 2 is moved inside with the rear side thereof being adjacent the anoderm 37. The inner side 7 of the bulge 6 faces the hemorrhoidal tissue. The light-dispensing means 14 is directed towards the anoderm and emits light shining through the anoderm 37.

In the selected illustration the suction pump 27 is not yet activated, so that the hemorrhoidal tissue 36 hardly enters into the cavity 8 thereby being disposed apart from the resection surface 12. Arrow 39 illustrates the direction of movement of the hemorrhoidal tissue 36 when the suction pump 27 is operating and the tissue 36 is drawn towards the resection surface 12 by means of negative pressure. The healthy parts of the tissue such as muscles and the rectum 31 attached thereto are thereby usually tensioned and do not follow the suction movement. Only bad hemorrhoidal tissue 36 reaches the resection surface 12, where it is resected.

In the following the operation and function of the embodiment of the inventive resection instrument illustrated in the drawing during the resection of hemorrhoids is explained in more detail.

In preparation of the operation the blood supply is at first ligated by means of ligatures at an inner layer of the inner sphincter 33. In the following a small incision is produced in the basic area of the hemorrhoidal tissue close to skin 35. With its front end 11 the resection instrument 2 is introduced in a forward direction through the incision 38.

At first only the vibration-surgical tissue disintegration device, i.e. the ultrasonic unit 17, is used and the hemorrhoidal tissue is dissected and fragmented. This preferably takes place along the edge of the inner sphincter 32 on one side and directly underneath the anoderm 37 on the other side. The path of the front end 11 in the tissue is looked at and controlled by means of the light-dispensing means 14 in a diaphanoscopical manner from outside through the anoderm.

Upon the dissection and the fragmentation the resection means 13 is applied and the hemorrhoidal tissue is disintegrated and discharged by means of the rinsing system or suction system. The bulge 6 is thereby placed with its rear side 16 onto the anoderm 37 such that the inner side 7 of the bulge faces the hemorrhoidal tissue 36. Only when activating the suction pump 27 is the hemorrhoidal tissue drawn into the cavity 8 thereby contacting the resection surface 12 and is removed by means of the resection means 13.

The operation technique known as minimally invasive, subanodermal hemorrhoidectomy in detail described in G 298 03 143.4 can be performed with the resection instrument 2 according to the invention.

What is claimed is:

1. Resection instrument, especially for the minimally invasive, subanodermnal, submucous removal of hemorrhoidal tissue, comprising:
   a narrow oblong carrier means provided with a resection portion for removing tissue on a front part thereof, wherein the resection portion is provided with a trough-shaped bulge being curved in a convex manner and approximately spoon-shaped in the longitudinal section; and
   a resection surface provided with a resection means for resectioning tissue disposed thereon, the resection means being embedded on the inner side of the bulge and deviating from a longitudinal direction of the instrument wherein a peripheral portion of the spoon-shaped resection portion surrounds the resection means.

2. Instrument according to claim 1, wherein the carrier means comprises an approximately rod-shaped holding portion extending in the longitudinal direction and the bulge, deviating from the longitudinal direction, is designed in a fashion that it at least partly bends back to the longitudinal direction in a convex manner.

3. Instrument according to claim 2, wherein the bulge, starting at the holding portion, is provided with a first arch curved outwardly and deviating from the longitudinal direction and, joining the same, with a second arch bent in a direction opposite to the first arch, at the inner side of which facing the longitudinal direction at least a part of the resection surface is provided.

4. Instrument according to claim 3, wherein the resection surface is exclusively limited to the area of the second arch.

5. Instrument according to claim 1, further comprising at least one suction opening to be connected to a negative pressure source is provided approximately in the area of the resection surface.

6. Instrument according to claim 2, wherein the resection portion is broader than the holding portion at least in the area of the bulge.

7. Instrument according to claim 1, wherein the bulge has a flat configuration in the cross-section relative to a holding portion of the carrier means.

8. Instrument according to claim 1, further comprising a light-dispensing means is provided on the rear side of the resection portion facing away from the inner side.

9. Instrument according to claim 1, further comprising light-dispensing means disposed at a front end of the resection portion.

10. Instrument according to claim 1, wherein a front end of the resection portion is provided with an ultrasonic unit for dissecting and fragmenting tissue.

11. Instrument according to claim 1, wherein the resection portion is configured as an ultrasonic vibration tissue disintegration device for dissecting and fragmenting tissue.

12. Instrument according to claim 1, further comprising a rinsing opening in the resection portion joining a rinsing channel to be connected to a rinsing system.

13. Instrument according to claim 12, wherein the rinsing opening is provided proximate the resection surface.

14. A resection instrument, comprising:
    an elongated holder portion having a longitudinal axis;
    a curved terminal portion having a substantially convex shape with respect to the longitudinal axis to define a cavity, the terminal portion being elongated in a direction transverse to the longitudinal axis; and
    a resection device having a resection surface to resect tissue, the resection device being embedded within the cavity along the resection surface in a location deviating from the longitudinal axis wherein a peripheral portion of the terminal portion surrounds the resection device.

15. The instrument of claim 14 wherein the curved terminal portion, starting at the holder portion, is provided with a first arch curved outwardly and deviating from the longitudinal axis and is further provided with a second arch bent in a direction opposite to the first arch, at the inner side of which facing the longitudinal axis, at least a part of the resection device is provided.

16. The instrument of claim 14, further comprising at least one suction opening to be connected to a negative pressure source is provided approximately in the area of the resection device.

17. The instrument of claim 14 wherein the resection device is configured as an ultrasonic vibration tissue disintegration device for dissecting and fragmenting tissue.

* * * * *